United States Patent
Nakagawa et al.

(10) Patent No.: US 10,702,133 B2
(45) Date of Patent: Jul. 7, 2020

(54) IMAGE PROCESSING DEVICE, ENDOSCOPE SYSTEM, IMAGE PROCESSING METHOD, AND COMPUTER-READABLE RECORDING MEDIUM

(71) Applicant: OLYMPUS CORPORATION, Tokyo (JP)

(72) Inventors: Hironori Nakagawa, Hachioji (JP); Yuji Kutsuma, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 81 days.

(21) Appl. No.: 16/167,648

(22) Filed: Oct. 23, 2018

(65) Prior Publication Data
US 2019/0053694 A1  Feb. 21, 2019

Related U.S. Application Data (63) Continuation of application No. PCT/JP2017/014271, filed on Apr. 5, 2017.

(30) Foreign Application Priority Data

Jun. 7, 2016  (JP) .................... 2016-113455

(51) Int. Cl.
*A61B 1/00* (2006.01)
*A61B 1/045* (2006.01)
(Continued)

(52) U.S. Cl.
CPC ........ *A61B 1/00181* (2013.01); *A61B 1/0005* (2013.01); *A61B 1/00009* (2013.01);
(Continued)

(58) Field of Classification Search
CPC combination set(s) only.
See application file for complete search history.

(56) References Cited

U.S. PATENT DOCUMENTS

2013/0076879 A1*  3/2013  On .................... A61B 1/00009
                                                                       348/65
2015/0265136 A1   9/2015  Honda
(Continued)

FOREIGN PATENT DOCUMENTS

JP   H01-185239 A   7/1989
JP   2013-066648 A  4/2013
(Continued)

OTHER PUBLICATIONS

International Search Report dated May 30, 2017 issued in PCT/JP2017/014271.
(Continued)

*Primary Examiner* — Janese Duley
(74) *Attorney, Agent, or Firm* — Scully, Scott, Murphy & Presser, P.C.

(57) ABSTRACT

An image processing device includes a processor including hardware. The processor is configured to: acquire an image data including an annular side observation image and a direct view observation image forming a circle formed from a center of the side observation image to an inner circle; in a case of normal observation in which electronic zooming processing is not performed, generate a first display image including a boundary portion between the side observation image and the direct view observation image in a display area; and in a case of magnified observation in which the electronic zooming processing is performed, generate a second display image in which a boundary portion between the side observation image and the direct view observation image is shielded by a mask.

11 Claims, 8 Drawing Sheets

(51) Int. Cl.
   *G02B 23/24* (2006.01)
   *H04N 5/232* (2006.01)
   *A61B 1/05* (2006.01)

(52) U.S. Cl.
   CPC .......... *A61B 1/00188* (2013.01); *A61B 1/045* (2013.01); *A61B 1/05* (2013.01); *G02B 23/2484* (2013.01); *H04N 5/23296* (2013.01); *A61B 1/00177* (2013.01)

(56) References Cited

U.S. PATENT DOCUMENTS

| | | |
|---|---|---|
| 2017/0085762 A1 | 3/2017 | Obara et al. |
| 2017/0215710 A1 | 8/2017 | Kura et al. |
| 2017/0257540 A1* | 9/2017 | Shiramizu ............ H04N 5/2256 |

FOREIGN PATENT DOCUMENTS

| | | |
|---|---|---|
| WO | WO 2011/055614 A1 | 5/2011 |
| WO | WO 2014/088076 A1 | 6/2014 |
| WO | WO 2016/072237 A1 | 5/2016 |
| WO | WO 2016/084522 A1 | 6/2016 |

OTHER PUBLICATIONS

JP Notification of Reasons for Refusal dated Feb. 14, 2018 issued in JP 2017-560644.

\* cited by examiner

IMAGE PROCESSING DEVICE, ENDOSCOPE SYSTEM, IMAGE PROCESSING METHOD, AND COMPUTER-READABLE RECORDING MEDIUM

CROSS REFERENCES TO RELATED APPLICATIONS

This application is a continuation of PCT international application Ser. No. PCT/JP2017/014271 filed on Apr. 5, 2017 which designates the United States, incorporated herein by reference, and which claims the benefit of priority from Japanese Patent Applications No. 2016-113455, filed on Jun. 7, 2016, incorporated herein by reference.

BACKGROUND

1. Technical Field

The present disclosure relates to an image processing device, an endoscope system, an image processing method, and a computer-readable recording medium for performing image processing on image data.

2. Related Art

In the related art, in an endoscope, there has been known a technique (see WO 2014/088076 A) to acquire an annular side observation image formed by capturing a side view field in a circumferential direction of an insertion portion by a side observation unit provided closer to a distal end of the insertion portion to be inserted into a subject, and a circular direct view observation image generated by capturing a front view field in an insertion direction of the insertion portion by a direct view observation unit provided closer to the distal end of the insertion portion than the side observation unit. In this technique, a shielding mask portion that shields a circumferential visual field region which cannot be imaged by the side observation unit is superimposed on a combined image obtained by combining a side observation image in a circumferential direction of the direct view observation image, a mask portion for chamfering is further superimposed on the four corners of the combined image, and the combined image is shaped into a rectangular shape and is displayed on a display monitor.

SUMMARY

Figure 6A:
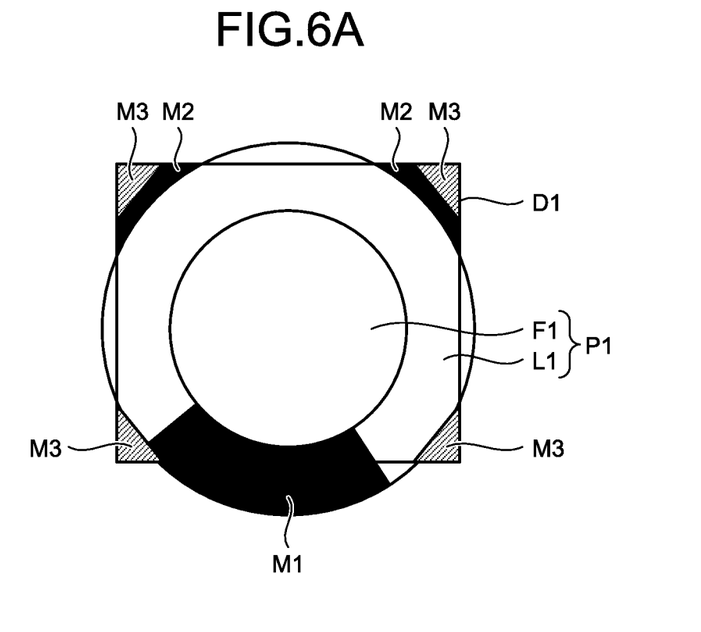
FIG. 6A is a diagram illustrating an example of an image in which a mask portion is superimposed on an endoscope.
Figure 6B:
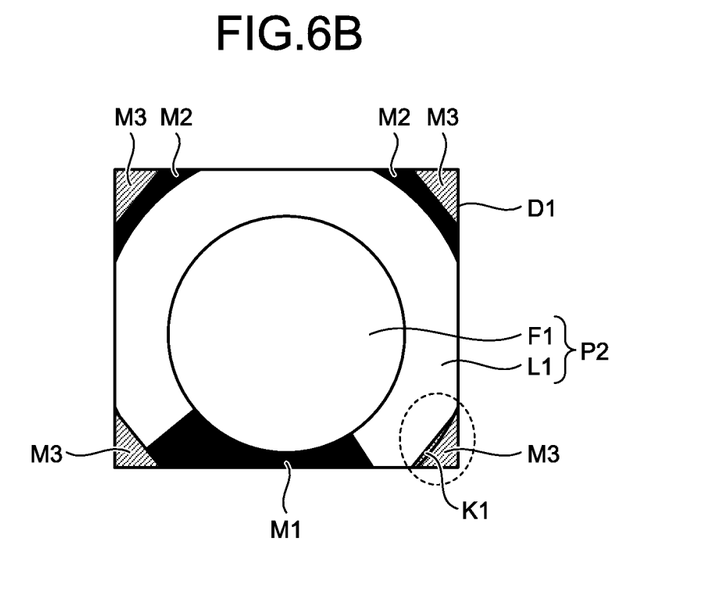
FIG. 6B is a diagram illustrating an example of an image in which the mask portion is superimposed on a display monitor.

However, in WO 2014/088076 A described above, since a shielding area of the mask portion is always constant regardless of an observation state, when performing normal observation, a part of the side observation image is shielded, and an observation field of view becomes narrow. Specifically, in the above-described WO 2014/088076 A, as illustrated in FIG. 6A, each of chamfered areas of a mask portion M1, a mask portion M2, and a mask portion M3 is always constant. Therefore, in the case of performing normal observation, when a combined image P1 obtained by combining a direct view observation image F1 with a side observation image L1 is displayed on a display monitor of a display area D1, as illustrated in FIG. 6B, the mask portion M3 becomes an image P2 in which a part K1 of the side observation image L1 is shielded, resulting in a narrowing of the observation field of view.

Figure 7A:
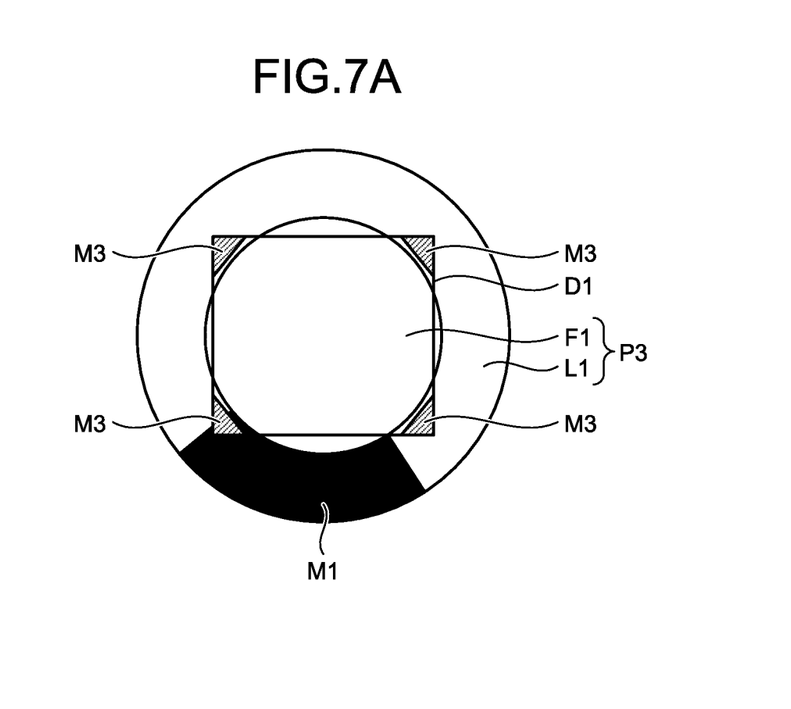
FIG. 7A is a diagram illustrating an example of an image obtained by combining the mask portion at the time of electronic zooming by the endoscope.
Figure 7B:
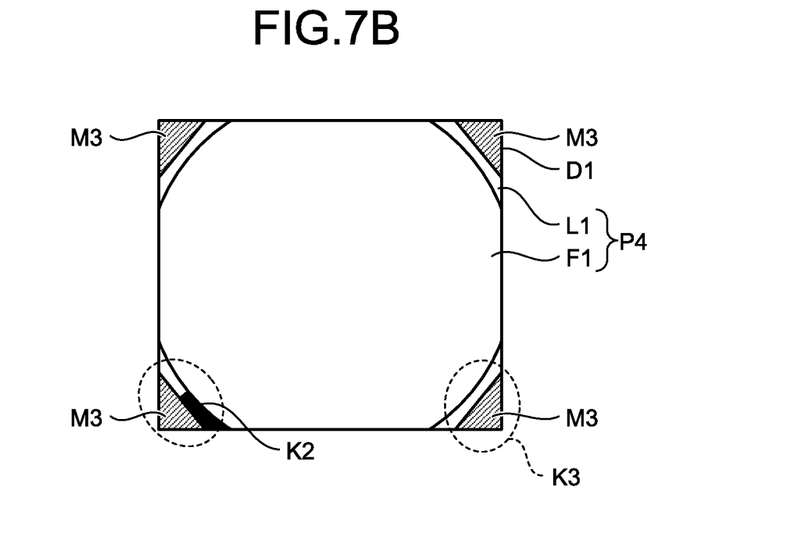
FIG. 7B is a diagram illustrating an example of an image obtained by combining the mask portion at the time of electronic zooming by the display monitor.

Furthermore, in the above-mentioned WO 2014/088076 A, there has been a problem that, when enlarged observation is performed by electronic zooming, a boundary line between the direct view observation image and the side observation image and an unclear area such as a step between the shielding mask portion and the mask portion move from the vicinity of the center of the display area toward the outer edge in accordance with the zoom magnification of an electronic zooming, whereby it is difficult to distinguish whether it is a lesion or a boundary when a user performs observation. Specifically, in the above-described WO 2014/088076 A, as illustrated in FIGS. 7A and 7B, there has been a problem that, when enlarged observation is performed by electronic zooming, when a combined image P3 obtained by combining the direct view observation image F1 and the side observation image L1 is displayed on the display monitor of the display area D1, an unclear area such as a boundary line K3 between the direct view observation image F1 and the side observation image L1 and a step K2 between the mask portions is an image P4 moved from the vicinity of the center of the display area D1 toward the outer edge side, whereby it is difficult to distinguish whether it is a lesion or a boundary when a user performs observation.

SUMMARY

In some embodiments, an image processing device includes a processor including hardware. The processor is configured to: acquire an image data including an annular side observation image formed by capturing a side view field in a circumferential direction of an insertion portion of an endoscope to be inserted into a subject, and a direct view observation image generated by capturing a front view field in an insertion direction of the insertion portion, the direct view observation image forming a circle formed from a center of the side observation image to an inner circle; in a case of normal observation in which electronic zooming processing that expands the image data to a predetermined magnification is not performed, generate a first display image including a boundary portion between the side observation image and the direct view observation image in a display area; and in a case of magnified observation in which the electronic zooming processing is performed, generate a second display image in which a boundary portion between the side observation image and the direct view observation image is shielded by a mask.

In some embodiments, an endoscope system includes: the image processing device; the endoscope; and a display.

In some embodiments, provided is an image processing method executed by an image processing device. The method includes: acquiring an image data including an annular side view observation image formed by capturing a side view field in a circumferential direction of an insertion portion of an endoscope to be inserted into a subject, and a direct view observation image generated by capturing a front view field in an insertion direction of the insertion portion, the direct view observation image forming a circle formed from a center of the side observation image to an inner circle; in a case of normal observation in which electronic zooming processing that expands the image data to a predetermined magnification is not performed, generating a first display image including a boundary portion between the side observation image and the direct view observation image in a display area; and in a case of magnified observation in which the electronic zooming processing is performed, generating a second display image in which a boundary portion between the side observation image and the direct view observation image is shielded by a mask.

In some embodiments, provided is a non-transitory computer-readable recording medium with an executable program stored thereon. The program causes an image processing device to execute: acquiring an image data including an annular side view observation image formed by capturing a side view field in a circumferential direction of an insertion portion of an endoscope to be inserted into a subject, and a direct view observation image generated by capturing a front view field in an insertion direction of the insertion portion, the direct view observation image forming a circle formed from a center of the side observation image to an inner circle; in a case of normal observation in which electronic zooming processing that expands the image data to a predetermined magnification is not performed, generating a first display image including a boundary portion between the side observation image and the direct view observation image in a display area; and in a case of magnified observation in which the electronic zooming processing is performed, generating a second display image in which a boundary portion between the side observation image and the direct view observation image is shielded by a mask.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, a mode for carrying out the disclosure (hereinafter referred to as "embodiment") will be described. In the embodiment, an endoscope system including an image processing device according to the disclosure will be described as an example. It should be noted that the disclosure is not limited by this embodiment. Further, in the description of the drawings, the same portions will be described with the same reference numerals.

Configuration of Endoscope System

Figure 1:
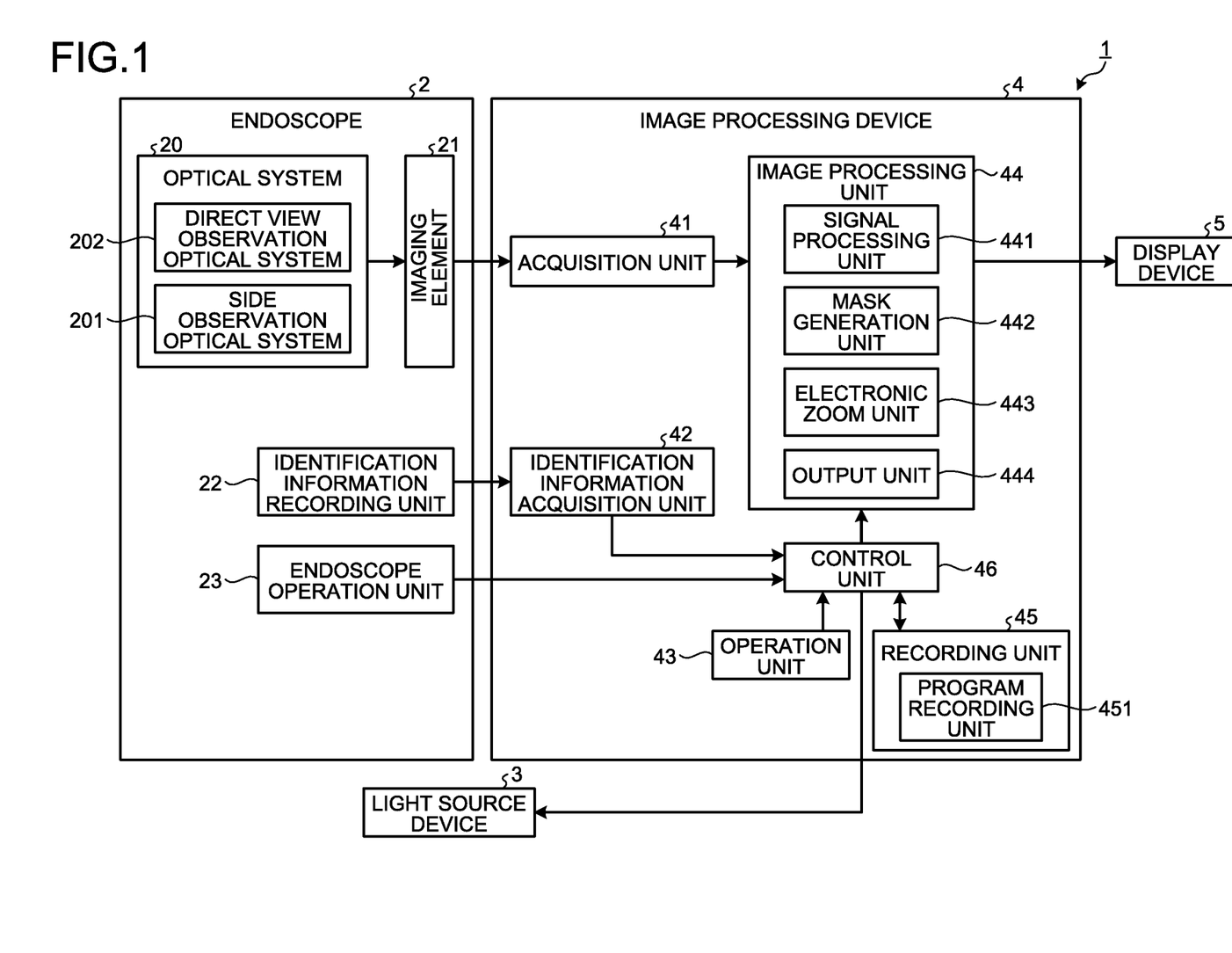
FIG. 1 is a block diagram illustrating a functional configuration of an endoscope system according to a first embodiment of the disclosure.

FIG. 1 is a block diagram illustrating a functional configuration of an endoscope system according to one embodiment of the disclosure. An endoscope system 1 illustrated in FIG. 1 includes an endoscope 2 (endoscope scope) that is inserted into a subject to capture the inside of the body of the subject to generate image data, a light source device 3 that irradiates the inside of the subject with illumination light via the endoscope 2, a light source device 3 that irradiates the inside of the subject with illumination light via the endoscope 2, an image processing device 4 (processor) that performs various processing on the image data input from the endoscope 2, and a display device 5 that displays an image corresponding to the image data input from the image processing device 4.

Configuration of Endoscope

First, the detailed configuration of the endoscope 2 will be described.

When the endoscope 2 is inserted into the subject, the endoscope 2 images the inside of the subject to generate image data. The endoscope 2 includes an optical system 20, an imaging element 21, an identification information recording unit 22, and an endoscope operation unit 23.

The optical system 20 includes a side observation optical system 201 that forms a subject image (hereinafter referred to as "side observation image") of an observation target in a circumferential side view field of the insertion portion, on a light receiving surface of an imaging element 21, the side observation optical system 201 being provided closer to a distal end of the insertion portion to be inserted into the subject, and a direct view observation optical system 202 that forms an object image (hereinafter referred to as a "direct view observation image") of an observation target in a front view field in the insertion direction of the insertion section, on the light receiving surface of the imaging element 21, the direct view observation optical system 202 being provided closer to the distal end of the insertion portion than the side observation optical system 201. The side observation image forms an annular shape. In addition, the direct view observation image forms a circle formed from the center of the side observation image to the inner circle. In the first embodiment, the side observation optical system 201 functions as a side observation unit and the direct view observation optical system 202 functions as a direct view observation unit.

The imaging element 21 receives each of the side observation image and the direct view observation image on the light receiving surface and performs photoelectric conversion to generate image data. The imaging element 21 is configured using imaging sensors such as a charge coupled device (CCD) and a complementary metal oxide semiconductor (CMOS).

The identification information recording unit 22 records identification information for identifying the endoscope 2. Here, the identification information includes an endoscope ID for identifying the endoscope 2, the angle of view of the endoscope 2, the model year of the endoscope 2, type information indicating the type of the endoscope 2, specification information of the endoscope 2, a method of transmitting image data of the endoscope 2, the transmission rate of the image data of the endoscope 2, information on observation light of a light source device 3 corresponding to the endoscope 2, and type information of the image processing device 4 that the endoscope 2 can deal with. The identification information recording unit 22 is realized by using, for example, a read only memory (ROM), a Flash memory, or the like.

The endoscope operation unit 23 receives inputs of various operations related to the endoscope 2. For example, the endoscope operation unit 23 receives inputs such as an instruction signal for switching observation light of the light source device 3, an instruction signal for instructing magnified observation by electronic zooming, and an instruction signal for instructing a freeze image (still image) by the endoscope 2, and outputs the received instruction signal to the image processing device 4. The endoscope operation unit 23 is configured using a plurality of switches.

Configuration of Light Source Device

Next, the configuration of the light source device 3 will be described.

Under the control of the image processing device 4, the light source device 3 successively switches and outputs a plurality of mutually different illumination light beams via the endoscope 2. The light source device 3 is configured with a white a light emitting diode (LED), and a color filter through which each of red, green, and blue light is transmitted. Note that the light source device 3 may be configured using a red LED, a green LED, and a blue LED.

Configuration of Image Processing Device

Next, the configuration of the image processing device 4 will be described.

The image processing device 4 includes an acquisition unit 41, an identification information acquisition unit 42, an operation unit 43, an image processing unit 44, a recording unit 45, and a control unit 46.

The acquisition unit 41 acquires image data from the endoscope 2 and outputs the acquired image data to the image processing unit 44.

The identification information acquisition unit 42 acquires the identification information of the endoscope 2 connected to the image processing device 4 from the identification information recording unit 22 of the endoscope 2 and outputs the acquired identification information to the control unit 46.

The operation unit 43 receives inputs of various operations related to the endoscope system 1. For example, the operation unit 43 receives inputs such as an instruction signal for switching observation light of the light source device 3, an instruction signal for instructing magnified observation by electronic zooming, and an instruction signal for instructing a freeze image (still image) by the endoscope 2, and outputs the received instruction signal to the control unit 46. The operation unit 43 is configured using a plurality of switches.

The recording unit 45 is realized by using a ROM, and records image data input from the endoscope 2, data including various parameters required for the operation of the endoscope system 1, and the like. Further, the recording unit 45 has a program recording unit 451 configured to record various programs executed by the endoscope system 1.

The image processing unit 44 is realized by using an FPGA or the like, performs various image processing on the image data input from the acquisition unit 41, and outputs the image data to the display device 5. The image processing unit 44 includes a signal processing unit 441, a mask generation unit 442, an electronic zoom unit 443, and an output unit 444.

The signal processing unit 441 performs predetermined signal processing on the image data. Here, the predetermined image processing includes, for example, synchronization processing, optical black reduction processing, white balance adjustment processing, color matrix calculation processing, gamma correction processing, color reproduction processing, edge enhancement processing, and format conversion processing.

Under the control of the control unit 46, the mask generation unit 442 generates a mask portion that masks the four corners of an image corresponding to image data that has been subjected to signal processing by the signal processing unit 441. Specifically, in the case of normal observation in which the electronic zoom unit 443 does not perform electronic zooming, the mask generation unit 442 generates a first mask portion that shields the outer side from the outer periphery of the side observation image. Further, in the case of magnified observation in which the electronic zoom unit 443 performs electronic zooming, the mask generation unit 442 generates a second mask portion that shields a boundary between the side observation image and the direct view observation image. For example, the mask generation unit 442 generates a second mask portion that shields an area connecting two points where the direct view observation image and a display area of a display device 6 intersect with each other with each vertex of the display area of the display device 6.

Under the control of the control unit 46, the electronic zoom unit 443 executes electronic zooming that expands an image corresponding to the image data that has been subjected to signal processing by the signal processing unit 441 to a predetermined magnification by performing trimming processing on the image.

Under the control of the control unit 46, the output unit 444 combines a mask portion generated by the mask generation unit 442 with an in-vivo image subjected to signal processing by the signal processing unit 441 to generate a first display image formed in accordance with a shape of a rectangular display area smaller than an image possessed by the display device 5, and outputs the generated first display image to the display device 5. Furthermore, when the endoscope 2 performs magnified observation by electronic zooming, under the control of the control unit 46, the output unit 444 combines, with an image enlarged by the electronic zoom unit 443 with electronic zooming, the second mask portion having a shielding area generated by the mask generation unit 442 according to electronic zooming to generate a second display image formed in accordance with a shape of a display area possessed by the display device 5, and outputs the generated second display image to the display device 5. Note that in the first embodiment, the output unit 444 functions as an image generation unit.

The control unit 46 is configured by using a central processing unit (CPU) or the like, and totally controls each unit of the endoscope system 1. The control unit 46 controls each unit of the endoscope system 1 according to an instruction signal input from the endoscope operation unit 23 or an instruction signal input from the operation unit 43.

Configuration of Display Device

Next, the configuration of the display device 5 will be described.

The display device 5 displays an image subjected to image processing by the image processing device 4 and various information related to the endoscope system 1. The display device 5 has a rectangular display area smaller than the image corresponding to the image data generated by the endoscope 2. The display device 5 is realized by using a display monitor having liquid crystal, organic electro luminescence (EL) or the like.

Processing of Image Processing Device

Figure 2:
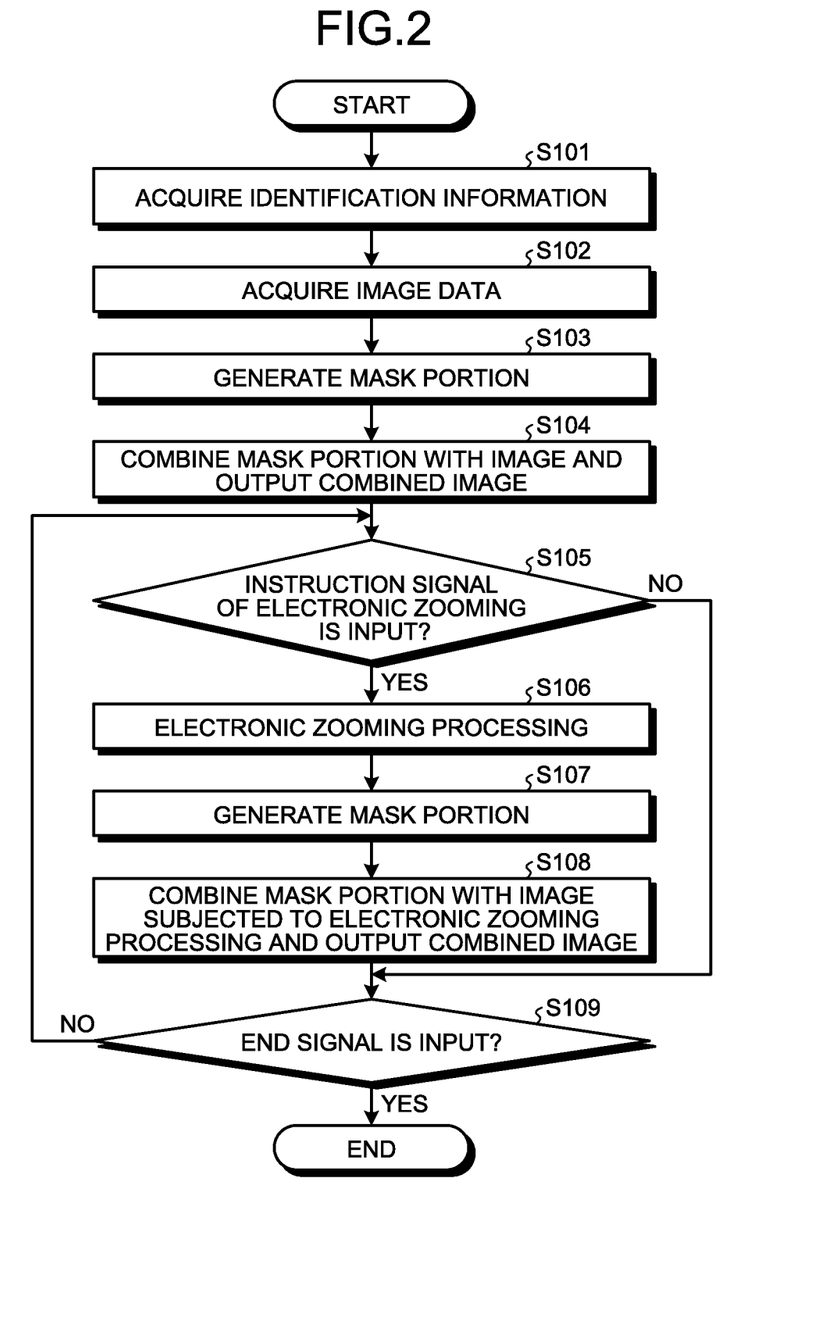
FIG. 2 is a flowchart illustrating an outline of processing executed by an image processing device according to the first embodiment of the disclosure.

Next, processing executed by the image processing device 4 will be described. FIG. 2 is a flowchart illustrating an outline of processing executed by the image processing device 4.

As illustrated in FIG. 2, first, the identification information acquisition unit 42 acquires identification information from the endoscope 2 connected to the image processing device 4, and outputs the acquired identification information to the control unit 46 (step S101).

Figure 3A:
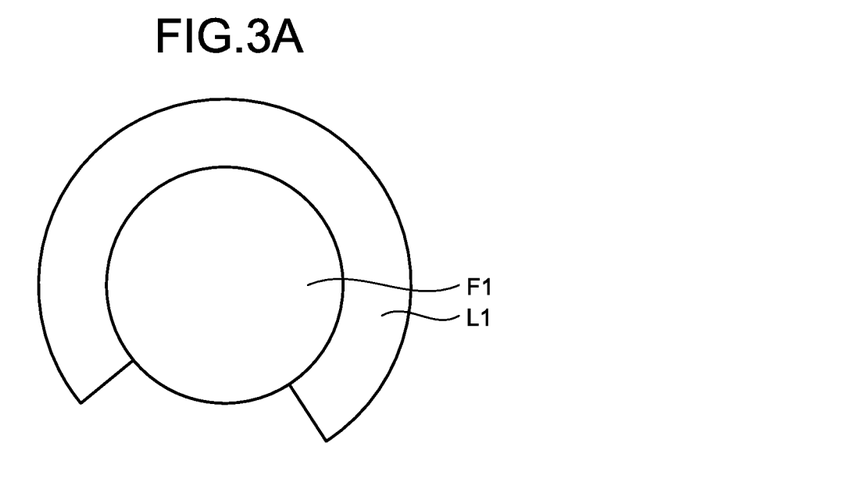
FIG. 3A is a diagram schematically illustrating an example of an image corresponding to image data generated by an endoscope according to the first embodiment of the disclosure.

Subsequently, the acquisition unit 41 acquires image data from the imaging element 21 of the endoscope 2 and outputs the acquired image data to the image processing unit 44 (step S102). Specifically, as illustrated in FIG. 3A, the acquisition unit 41 acquires an image corresponding to image data including the side observation image L1 and the direct view observation image F1 from the imaging element 21 of the endoscope 2.

Figure 3B:
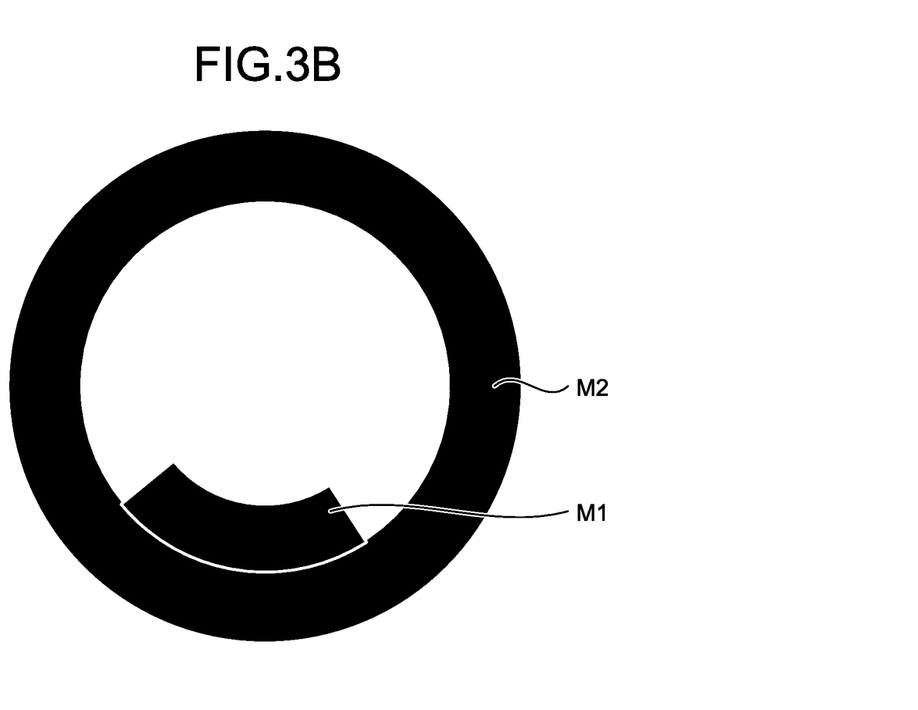
FIG. 3B is a diagram schematically illustrating a shape of a mask portion generated by a mask generation unit of the image processing device according to the first embodiment of the disclosure.

Thereafter, under the control of the control unit 46, the mask generation unit 442 generates a mask portion according to the identification information of the endoscope 2 (step S103). More specifically, as illustrated in FIG. 3B, the mask generation unit 442 generates a shielding mask portion M1 that shields a circumferential visual field area which cannot be imaged by the side observation unit, and an annular mask portion M2 chamfering a circumferential direction of the side observation image L1. In the present embodiment, the mask portion M2 functions as a first mask.

Figure 3C:
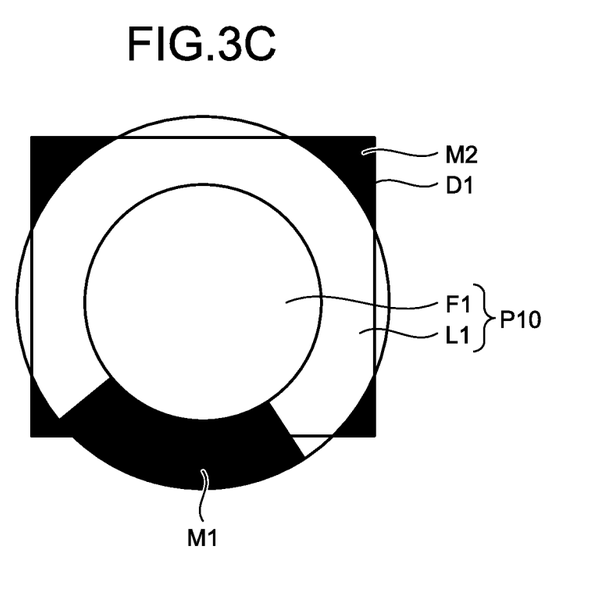
FIG. 3C is a diagram schematically illustrating a state in which an output unit of the image processing device according to the first embodiment of the disclosure combines the mask portion with an image.
Figure 3D:
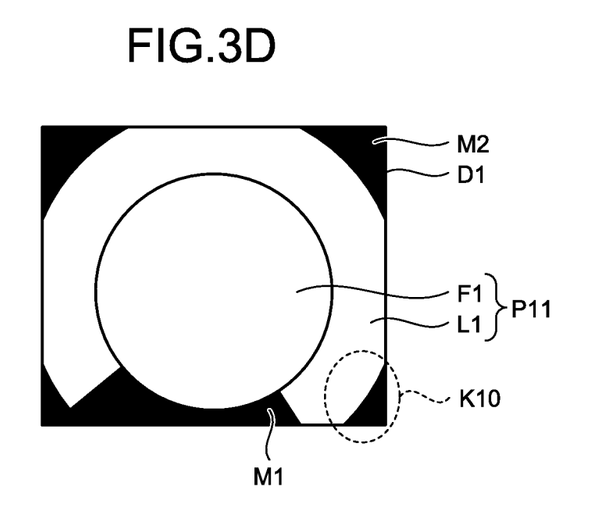
FIG. 3D is a diagram illustrating an example of an image displayed by a display device according to the first embodiment of the disclosure.

Subsequently, the output unit 444 combines the mask portion generated by the mask generation unit 442 with the image corresponding to the image data, and outputs the combined image to the display device 5 (step S104). Specifically, as illustrated in FIG. 3C, the output unit 444 combines the shielding mask portion M1 and the mask portion M2 generated by the mask generation unit 442 with the image P10 corresponding to the image data including the side observation image L1 and the direct view observation image F1, and outputs a first display image formed (subjected to trimming processing) in accordance with the shape of the rectangular display area D1 smaller than the image P10 possessed by the display device 5. As a result, as illustrated in FIG. 3D, the display device 5 can display the first display image P11 including an area K10 where the side observation image L1 of the side view field is not shielded by the mask portion M2. As a result, the observation field of view of the endoscope 2 can be maintained.

Thereafter, when an instruction signal instructing electronic zooming is input from the endoscope operation unit 23 or the operation unit 43 (step S105: Yes), the image processing device 4 proceeds to step S106 described later. On the other hand, when the instruction signal for instructing electronic zooming is not input from the endoscope operation unit 23 or the operation unit 43 (step S105: No), the image processing device 4 proceeds to step S109 described later.

In step S106, the electronic zoom unit 443 performs electronic zooming processing for enlarging the image data to a predetermined magnification by performing trimming processing on the image data.

Subsequently, the mask generation unit 442 generates a mask portion that shields a boundary between the side observation image and the direct view observation image in accordance with the zoom magnification of electronic zooming to chamfer the image (step S107).

Figure 4A:
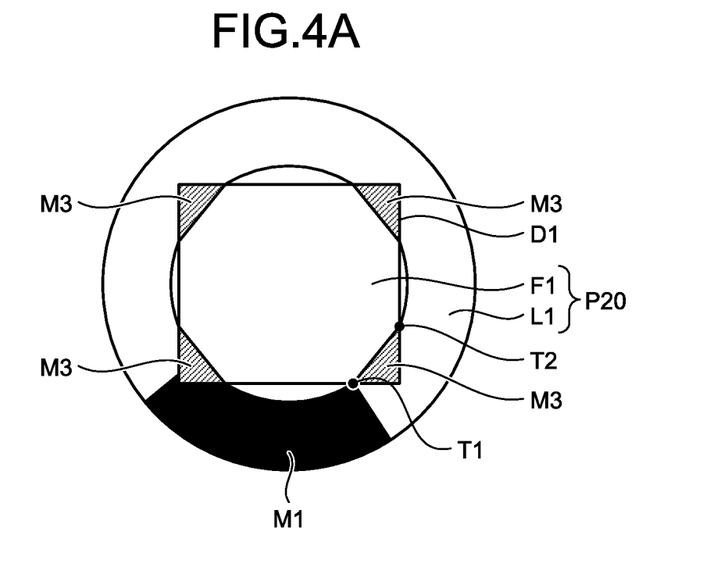
FIG. 4A is a diagram schematically illustrating a state in which the output unit of the image processing device according to the first embodiment of the disclosure combines the mask portion with an image at the time of electronic zooming of the endoscope.
Figure 4B:
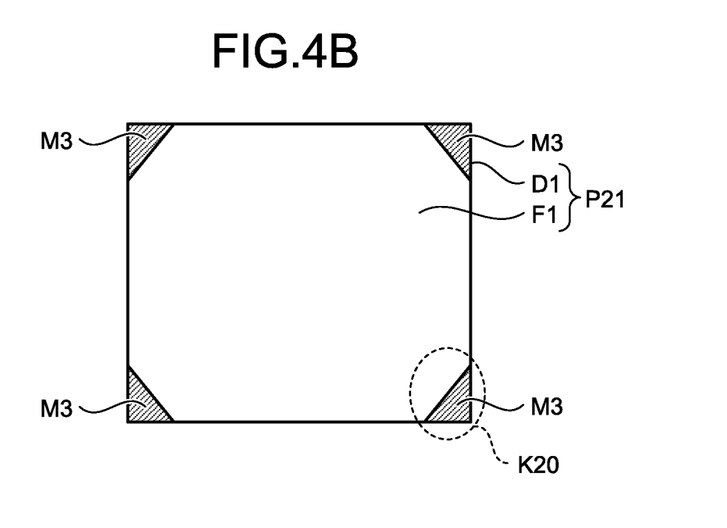
FIG. 4B is a diagram illustrating an example of an image displayed by the display device according to the first embodiment of the disclosure at the time of electronic zooming of the endoscope.

Thereafter, the output unit 444 combines the mask portion generated by the mask generation unit 442 with the image subjected to the electronic zooming processing by electronic zoom unit 443, and outputs the combined image to the display device 5 (step S108). Specifically, as illustrated in FIG. 4A, the output unit 444 combines a mask portion M3 generated by the mask generation unit 442 with the image P20 subjected to electronic zooming processing by the electronic zoom unit 443, generates a second display image formed in accordance with the shape of the rectangular display area D1 smaller than an image P20 possessed by the display device 5 and outputs the second display image. More specifically, the output unit 444 combines, with each of four corners of the display area D1, the mask portion M3 (second mask portion) generated by the mask generation unit 442, the mask portion M3 having a triangle shape that shields an area formed by two points (point T1 and point T2) where the direct view observation image F1 and the display area D1 intersect with each other and the display area D1. Thus, as illustrated in FIG. 4B, the display device 5 can display a second display image P21 in which an ambiguous boundary area K20 between the side observation image L1 and the direct view observation image F1 is shielded by the mask portion M3. As a result, it is possible to prevent diagnostic judgment from being made in an ambiguous boundary area between the side observation image L1 and the direct view observation image F1 when the user performs observation.

Subsequently, when an end signal instructing the end of observation is input from the endoscope operation unit 23 or the operation unit 43 (step S109: Yes), the image processing device 4 ends the present processing. On the other hand, when the end signal instructing the end of the observation has not been input from the endoscope operation unit 23 or the operation unit 43 (step S109: No), the image processing device 4 proceeds to the above-described step S105.

According to the embodiment of the disclosure described above, in the case where the output unit 444 is in normal observation, the output unit 444 combines the mask portion M2 with the image P10 to generate and display the first display image P11 formed in accordance with the shape of the rectangular display area possessed by the display device 5, and on the other hand, in the case of magnified observation, the output unit 444 combines the mask portion M3 with the image P20 enlarged by the electronic zoom unit 443 to generate the second display image P21 formed in accordance with the shape of the display area D1 and output the second display image P21 to the display device 5, so that it is possible to prevent the observation field of view from narrowing regardless of the observation state and to shield an unclear area at the time of electronic zooming.

Modification

Figure 5A:
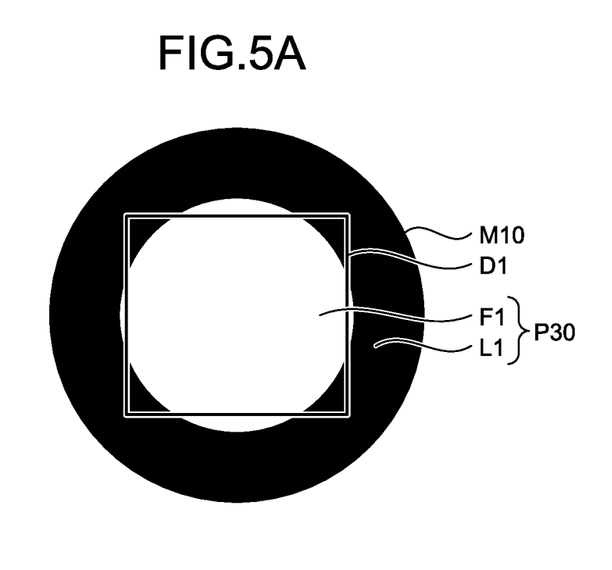
FIG. 5A is a diagram schematically illustrating a state in which the output unit of the image processing device according to a modification of the first embodiment of the disclosure combines the mask portion with an image at the time of electronic zooming of an endoscope system.
Figure 5B:
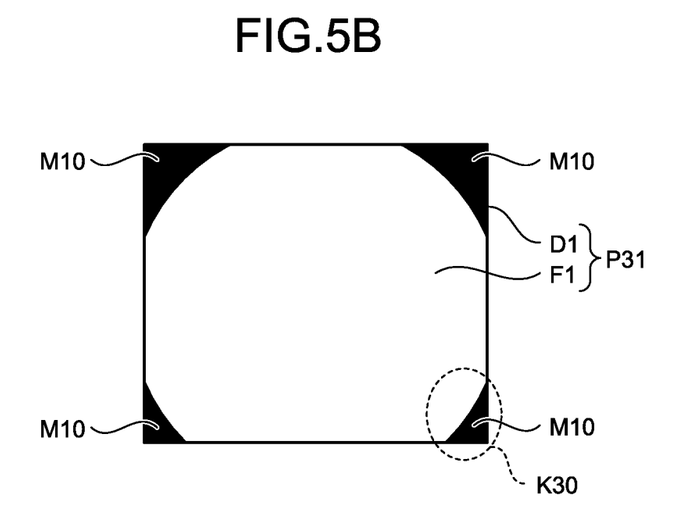
FIG. 5B is a diagram illustrating an example of an image displayed by the display device according to the modification of the first embodiment of the disclosure at the time of electronic zooming of the endoscope system.

Next, in the embodiment of the disclosure, in the case where the endoscope system 1 is performing electronic zooming, the mask generation unit 442 shields the four corners of the endoscopic image corresponding to the image data, so that the shape of the display image is an octagon; however, in the case where the endoscope system 1 is performing electronic zooming, an annular mask portion shielding all of the side view field may be generated, combined, and output. More specifically, as illustrated in FIG. 5A, the output unit 444 combines a circular mask portion M10 generated by the mask generation unit 442 with the image P30 subjected to electronic zooming processing by the electronic zoom unit 443, and displays the combined image on the display device 5. As a result, as illustrated in FIG. 5B, the display device 5 displays an image P31 in which an ambiguous boundary area K30 between the side observation image L1 and the direct view observation image F1 is shielded. Further, the side observation image L1 is entirely shielded by the mask portion M10. Accordingly, it is possible to prevent diagnostic judgment from being made in an ambiguous boundary area between the side observation image L1 and the direct view observation image F1 when the user performs observation.

Other Embodiments

Further, in the embodiment of the disclosure, the image data is transmitted to the image processing device via a transmission cable; however, for example, there is no need to transmit the image data by wire, and the image data may be transmitted wirelessly. In this case, image data or the like may be transmitted to the image processing device in accordance with a predetermined wireless communication standard (for example, Wi-Fi (registered trademark) or Bluetooth (registered trademark)). It is needless to say that wireless communication may be performed according to other wireless communication standards.

In the embodiments of the disclosure, the image processing device and the light source device are separate bodies, but the disclosure is not limited thereto. For example, the image processing device and the light source device may be integrally formed.

Further, in the embodiment of the disclosure, a sequential lighting endoscope has been described as an example, but a simultaneous lighting endoscope can also be applied.

Further, in the embodiment of the disclosure, the endoscope is inserted into the subject, but the disclosure can also be applied to, for example, a capsule endoscope or an imaging apparatus which captures the subject.

According to the disclosure, it is possible to prevent narrowing of an observation field of view regardless of an observation state, and to shield an unclear area at the time of electronic zooming.

In the description of the flowchart in the present specification, the context of each processing is clearly indicated by using expressions such as "first", "after", "followed by", or the like, the order of processing required for implementing the disclosure is not uniquely determined by these expressions. That is, the order of processing in the flowcharts described in the present specification can be changed within a range without inconsistency.

As described above, the disclosure can include various embodiments not described here, and it is possible to make various design changes and the like within the scope of the technical idea specified by the scope of claims.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising
a processor comprising hardware, wherein the processor is configured to:
acquire an image data including an annular side observation image formed by capturing a side view field in a circumferential direction of an insertion portion of an endoscope to be inserted into a subject, and a direct view observation image generated by capturing a front view field in an insertion direction of the insertion portion, the direct view observation image forming a circle formed from a center of the side observation image to an inner circle;
in a case of normal observation in which electronic zooming processing that expands the image data to a predetermined magnification is not performed, generate a first display image including a boundary portion between the side observation image and the direct view observation image in a display area; and
in a case of magnified observation in which the electronic zooming processing is performed, generate a second display image in which a boundary portion between the side observation image and the direct view observation image is shielded by a mask.

2. The image processing device according to claim 1, wherein
the processor is further configured to acquire the image data from an imaging sensor provided in the endoscope, and
the imaging sensor is configured to receive the side observation image and the direct view observation image on a light receiving surface and perform photoelectric conversion to generate the image data.

3. The image processing device according to claim 1, wherein the processor is further configured to:
in the case of the normal observation, generate a first mask portion configured to shield an outer side from an outer side of the side observation image, and combine the first mask portion with an image corresponding to the image data to generate a first display image formed in accordance with a shape of a rectangular display area possessed by a display; and
in the case of the magnified observation, generate a second mask portion configured to shield a boundary between the side observation image and the direct view observation image, and combine the second mask portion with an image enlarged by performing the electronic zooming processing to generate a second display image formed in accordance with a shape of the rectangular display area possessed by the display.

4. The image processing device according to claim 3, wherein the second mask portion is configured to shield an area connecting two points where the direct view observation image and the display area intersect with each other.

5. The image processing device according to claim 3, wherein the second mask portion is configured to shield an area formed by a straight line connecting two points where the direct view observation image and the display region intersect with each other and the display area.

6. The image processing device according to claim 3, wherein the second mask portion has an annular shape that shields the side observation image.

7. The image processing device according to claim 3, wherein the processor is further configured to change a shielded area of the second mask portion based on a magnification by the electronic zooming processing.

8. The image processing device according to claim 3, wherein the processor is further configured to output the first display image and the second display image to the display.

9. An endoscope system comprising:
the image processing device according to claim 1;
the endoscope; and
a display.

10. An image processing method executed by an image processing device, the method comprising:
acquiring an image data including an annular side view observation image formed by capturing a side view field in a circumferential direction of an insertion portion of an endoscope to be inserted into a subject, and a direct view observation image generated by capturing a front view field in an insertion direction of the insertion portion, the direct view observation image forming a circle formed from a center of the side observation image to an inner circle;
in a case of normal observation in which electronic zooming processing that expands the image data to a predetermined magnification is not performed, generating a first display image including a boundary portion between the side observation image and the direct view observation image in a display area; and
in a case of magnified observation in which the electronic zooming processing is performed, generating a second display image in which a boundary portion between the side observation image and the direct view observation image is shielded by a mask.

11. A non-transitory computer-readable recording medium with an executable program stored thereon, the program causing an image processing device to execute:
acquiring an image data including an annular side view observation image formed by capturing a side view field in a circumferential direction of an insertion portion of an endoscope to be inserted into a subject, and a direct view observation image generated by capturing a front view field in an insertion direction of the insertion portion, the direct view observation image forming a circle formed from a center of the side observation image to an inner circle;
in a case of normal observation in which electronic zooming processing that expands the image data to a predetermined magnification is not performed, generating a first display image including a boundary portion between the side observation image and the direct view observation image in a display area; and
in a case of magnified observation in which the electronic zooming processing is performed, generating a second display image in which a boundary portion between the side observation image and the direct view observation image is shielded by a mask.

* * * * *